United States Patent [19]

Strokosz et al.

[11] Patent Number: 5,893,528
[45] Date of Patent: Apr. 13, 1999

[54] TUBING RETRACTING SYSTEM

[75] Inventors: Arkadiusz A. Strokosz, Laguna Niguel; Lawrence J. Green, Huntington Beach; Philip O. Merritt, La Canada; Bradford H. Hack, Arcadia, all of Calif.

[73] Assignee: Pabban Development, Inc., Irvine, Calif.

[21] Appl. No.: 08/798,131

[22] Filed: Feb. 12, 1997

[51] Int. Cl.⁶ ............................................. B45H 75/48
[52] U.S. Cl. .................. 242/373; 242/385.1; 242/385.3
[58] Field of Search ......................... 242/373, 388.1, 242/385.3

[56] References Cited

U.S. PATENT DOCUMENTS

| | | | |
|---|---|---|---|
| 1,524,172 | 1/1925 | Dewey | 242/385.1 |
| 1,675,140 | 6/1928 | Schenderlein | 242/385.1 |
| 2,641,790 | 6/1953 | Coult | 242/385.1 |
| 3,486,712 | 12/1969 | Hoday | 242/385.1 |
| 3,895,764 | 7/1975 | Roland | 242/385.1 |
| 4,384,688 | 5/1983 | Smith | 242/385.1 |
| 5,094,396 | 3/1992 | Burke | 242/385.1 |
| 5,186,406 | 2/1993 | Romanelli | 242/373 |

FOREIGN PATENT DOCUMENTS

| | | | |
|---|---|---|---|
| 4-106078 | 4/1992 | Japan | 242/385.1 |
| 187887 | 2/1964 | Switzerland | 242/373 |

*Primary Examiner*—William Stryjewski
*Attorney, Agent, or Firm*—G. Donald Weber, Jr.

[57] ABSTRACT

A retracting system especially for use with operating room equipment and adapted to permit a vinyl tube to be removed from a storage spool to a desired length. The spool system is then locked into position so that the tubing is not retracted. By pulling slightly on the tubing, the apparatus retracts the tubing onto the storage spool for future utilization.

29 Claims, 2 Drawing Sheets

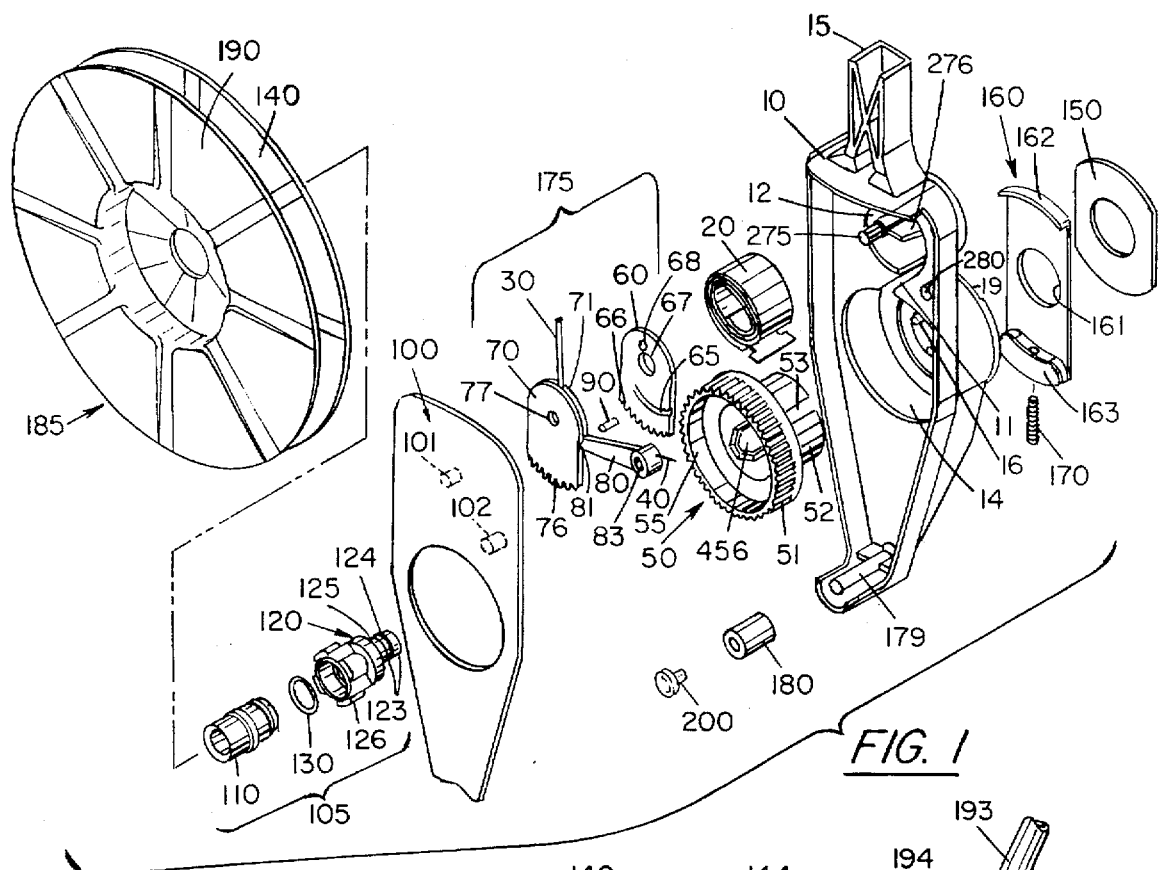
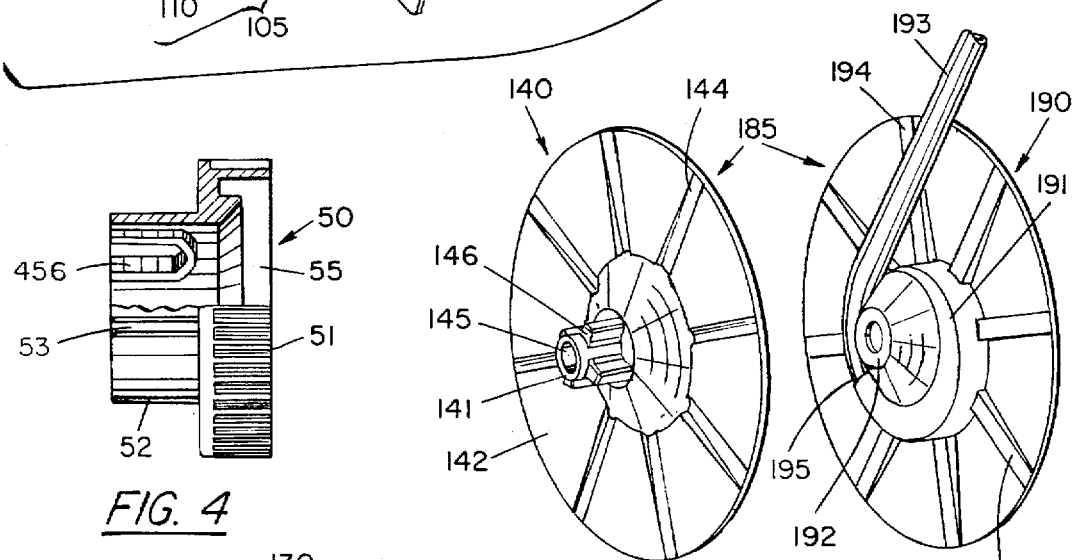

TUBING RETRACTING SYSTEM

BACKGROUND

1. Field of the Invention

This invention is directed to a vinyl tube or tubing supply system, in general, and to a supply system which selectively retracts the vinyl tubing onto a storage spool, in particular.

2. Prior Art

There are many known means for providing vinyl tubing to various types of devices especially when used in hospitals and, more particularly, in the operating rooms thereof. The vinyl tubes are used for many purposed including, but not limited to, suction, irrigation evacuation or the like.

In the past, the tubes or tubing have been connected to the appropriate sources such as suction pumps, liquid reservoirs and the like and arranged around the operating table in a rather haphazard fashion. For example, the tubing is frequently allowed to rest on the operating table, on the patient or the like. This has, of course, presented some difficulties in maintaining the sterile field of the medical procedure.

Moreover, the tubing is frequently in the way of the surgeon or other operating room personnel. The tubing frequently becomes a nuisance in that it interferes with the procedures being performed. In addition, if more than one tubing is in use, the tubing can become confused, entangled, intermingled and so forth.

SUMMARY OF THE INSTANT INVENTION

A retracting system especially for use with operating room equipment. The retracting system is adapted to permit a vinyl tube (or the like) to be removed from a storage spool to a desired and/or specified length. The spool system is then locked so that the tubing remains extended and is not retracted. However, by pulling slightly on the tubing, in the direction of extension, the apparatus retracts the tubing onto the storage spool for future utilization. A constant torque spring drive provides for a controlled retractio process.

BRIEF DESCRIPTION OF THE DRAWINGS

FIG. 1 is an exploded view of the apparatus of the instant invention.

FIG. 2 is an exploded view of the spool mechanism of the instant invention.

FIG. 3 is an exploded view of one embodiment of the seal/nipple connector.

FIG. 4 is a partially broken away view of the locking hub of the instant invention.

DESCRIPTION OF A PREFERRED EMBODIMENT

Referring now to FIG. 1, there is shown an exploded view of a preferred embodiment of the tubing retractor of the instant invention. The retractor system includes a spool 185 which includes a pair of parallel disks 190 and 140. The disks define a space therebetween for supporting the tubing which is to be stored and retracted as described hereinafter.

As will become apparent, in a preferred embodiment the spool 185 is adapted to incorporate the retractable tubing therein as an integral component thereof. Of course, this is not an absolute requirement of the invention.

Figure 2A:
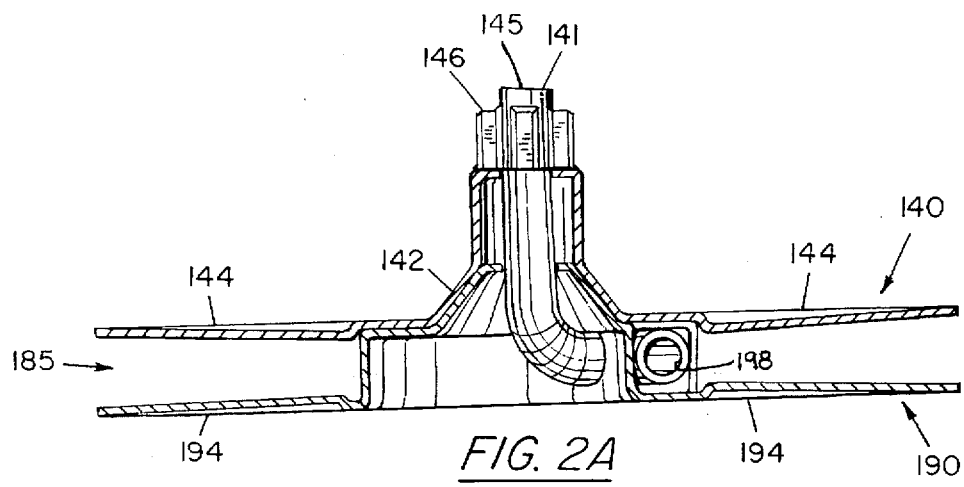
FIG. 2A is a cross-sectional view of the assembled spool mechanism of the instant invention.

As shown in FIG. 1, there is incorporated a rotating seal 110 which is connected to the spool 185 and rotates therewith. The seal 110 is mounted in a centrally located hub portion of disk 140. This hub portion (not visible in FIG. 1) includes splines as will be shown and described hereinafter relative to FIGS. 2 and 2A. It will be noted that these splines engage the drive hub 52 (part of motor hub 50) which is rotatably mounted in the housing 10 retractor mechanism as described hereinafter. As shown in FIGS. 2 and 2A, the spool 185 is adapted to specifically engage the inner surface of the drive hub 52 so that rotation of drive hub 52 and motor hub 50 causes rotation of spool 185 and vice versa.

A connecting nipple 120 is adapted to interact with and receive the rotating seal 110 therein to provide a leakproof seal between the tubing on the spool, as joined to the rotating seal, and the external pump or source described supra. A suitable O-ring 130 or the like forms a part of the seal between the rotating seal 110 and nipple 120. The nipple 120 includes at least one spline 126 and is adapted to detachably engage splines 16 which are formed in the rear surface of housing 10. Thus, the nipple 120 remains substantially stationary irrespective of rotation of the spool 185. The nipple 120 includes a locking groove 125 for engaging the sliding latch 160 as described infra.

The nipple 120 includes the axial extension which includes ridges 123 and groove 124. The extension is, thus, capable of snugly and securely engaging a tubing from a utilization source such as a pump, a resevoir or the like.

The motor hub 50 includes two coaxial cylindrical components, namely latching hub 55 and drive hub 52 which are integrally formed.

The drive hub 52 extends axially outwardly from the rear of motor hub 50. The drive hub 52 includes, on the inner surface thereof, the appropriate splines 146 (or the like) for engaging spool 185 as described hereinafter. The outer circumference of latching hub 55 includes a plurality of grooves or teeth 51 which are used to engage the toothed edges 66 and 76 of the hub latch 175 as described hereinafter. The hub latch 175 includes inner and outer latch plates 60 and 70, respectively. The latch 175 is rotatably mounted on the post 275 and supported by support web 276 (which also provides strength to post 275) as described infra.

The cam follower arm 80 is pivotably mounted on a suitable support post 280 in the retraction system housing 10 adjacent to lower cavity 14 and engages the cam grooves, e.g. groove 65 and 75 (see FIG. 7) on the inner surfaces of the inner and outer latch plates 60 and 70, respectively, as described hereinafter. A representative cam groove 65 is shown on the inner surface of latch plate 60. The cam follower arm 80 includes a cam follower arm positioning spring 40 which positions the cam follower appropriately in the housing 10. Likewise, the hub latch 175 includes a latch positioning spring 30 which positions the hub latch 175 in the appropriate position within housing 10 as described hereinafter. The springs 30 and 40 can be controlled by any suitable limit devices in housing 10.

A coil spring 20 is mounted in the retraction system housing 10 and is connected to the drive hub 52 of the motor hub 50 as described hereinafter. In particular, the coil spring 20 is disposed in an upper cavity 12 within the housing 10. The coil spring 20 passes through the slot 11 in housing 10 and engages drive hub 52 which is mounted in lower cavity 14 in housing 10. As noted (and described hereinafter), the internal surface of lower cavity 14 includes splines 16 (or notches) which receive and engage the splines on spool 185.

A sliding latch 160 is mounted in a groove 19 on the exterior surface of the housing 10 adjacent to lower cavity 14. The sliding latch 160 includes a latch spring 170 which is mounted in an aperture in one end of the sliding latch 160 and bears against a portion of housing 10, typically the outer surface of lower cavity 14. Latch spring 170 urges the sliding latch 160 into the locking position described hereinafter wherein the aperture 161 in the sliding latch 160 engages the locking groove 125 and locks the nipple 120 (and, thus, the spool 185) in the housing 10. The upper and lower lips 162 and 163, respectively, control the extent of the movement of sliding latch 160. The cover 150 is affixed to the outer surface of the housing 10 adjacent to lower cavity 14 and retains the sliding latch 160 in slidable relation to the housing 10 in groove 19.

In the embodiment shown in FIG. 1, the housing end 15 is formed to interact with a support bracket (not shown). The bracket can be mounted adjacent to the field of use for the tubing and retractor mechanism.

When assembled, the nipple 120, seal 110 and O-ring 130 are assembled and joined to the outlet of spool 185 (shown and described infra). The motor hub 50 (including latching hub 55 with attached drive hub 52) and the driving coil spring 20 are inserted into the cavities 14 and 12, respectively, in the housing 10. The hub latch 175 is also placed in the housing 10 on post 275 such that the toothed edges 66 and 76 are selectively in engagement with the teeth 51 of latching hub 55. The springs 40 and 30 bear against the inner walls of the housing 10 (or other suitable limit stops formed within housing 10) to, respectively, position the hub latch 175 and the cam follower arm 80 appropriately. The pin 90 is slidably mounted in the aperture 81 in the cam follower arm 80 and inserted into cam groove 61 in latch plate 60 and in counterpart slots in latch plate 70 (see infra).

The idler roller 180 is rotatably mounted on the roller shaft 179 in the housing 10 and secured in place by the screw 200 or the like. The housing cover 100 is then placed against the housing 10 such that pin 101 passes through the openings 67 and 77 in hub latch 175 and engages post 275. Likewise, pin 102 passes through aperture 83 in cam follower arm 80 and engages post 280. Housing cover 100 is then placed against the surfaces of the housing 10 and secured thereto in any suitable fashion such as sonic welding, gluing or the like.

Spool 185 is then mounted on the housing 10 by inserting the nipple 120 through the central opening in the hubs 55 and 52, the central opening in the rear surface of housing 10 and through the openings in sliding latch 160 and external cover 150. As described, the sliding latch 160 is spring loaded to engage the locking groove 125 in the nipple 120 to retain the spool 185 in contact with the housing 10. Also, the splines 126 on nipple 120 engage the splines 16 in housing 10 to prevent rotation of the nipple 120. A suitable axiliary tubing (not shown) can be connected to the end of nipple 120.

Also, as noted, the splined hub of spool 185 is now in interlocking engagement with the splines 146 on the inner surface of drive hub 52. Consequently, when tubing is withdrawn from spool 185, spool 185 rotates and drives drive hub 52 which is connected to coil spring 20 to produce a constant torque on the drive hub 52. Hub latch 175 engages the teeth 51 on latching hub 55 and maintains the motor hub 50 in the fixed position so that the tubing withdrawn from the spool 185 will remain extended until overtly released. The release of the spool 185 and, thus, the retraction of the tubing onto spool 185 is accomplished by exerting a relatively short pull or extension on the extended tubing. This short pull moves the spool 185 and drives the motor hub 50 slightly. Hub latch 175 moves therewith so that the cam follower arm 80 engages with the slots in hub latch 175 and, thereby, releases latching hub 55. When the hub is released from the latching action, the coil spring 20 rewinds whereby the hubs 55 and 52 are rotated counter to the direction in which the hub was driven when the spool 185 was operated to withdraw tubing. When the spool 185 is driven in the counter direction, the tubing is retracted and stored in the spool 185.

The spool 185 is located adjacent to the idler roller 180 wherein the juxtaposition of the roller and the spool substantially dictates that the tubing will be rewound on the spool 185 in the appropriate fashion.

In an alternative embodiment, the spool 185 and the seal/nipple connector 105 can be formed as an integral unit. In this case, the nipple does not rotate relative to the spool but together therewith. In this case, the splines 126 on the nipple, as well as the splines 16 in cavity 14, can be eliminated. The sliding latch 160 will still engage the locking groove 125 of the nipple portion of the integral unit.

Referring now to FIG. 2, there is shown an exploded view of the spool 185. This view is taken from the opposite side of spool 185 relative to the spool shown in FIG. 1. FIG. 2 shows the disk 190 including a spiral shaped interior hub 191 which includes a slightly conical shaped center 192. As will be apparent, the conical shaped center 192 nests within a conical cavity on the back of disk 140. The spiral shaped interior hub 191 is a channel which is adapted to engage the tubing 193 which can be a vinyl-type tubing or the like. The other end of the spiral shaped interior hub 191 ends in the conical shaped center 192 so that the tubing 193 communicates through the hollow spiral shaped interior 191 with the opening 195 in the conical shaped center 192 and, thus, into the central hub of disk 140. A plurality of ribs 194 extend radially outwardly from the center to the circumference of the disk 190 in order to provide structural strength to the disk.

The disk 140 includes a plurality of similar radially extending ribs 144 which impart physical strength to the disk. The central hub 142 of disk 140 is substantially conical shaped to accept and receive the conical shaped center 192 of disk 190. An external hub 141 is joined to the central hub 142 and includes an opening 145 through the center thereof. The opening 145 communicates with the opening 195 in disk 190 which communicates with the tubing 193 via the spiral shaped interior hub 191. As will be apparent, the opening 145 communicates with the hollow seal 110 shown in FIGS. 1 and 3. A plurality of splines 146 are spaced around the external hub 141 and extend radially outwardly therefrom. The splines 146 engage the internal splines 456 in the drive hub 52 shown in FIG. 1.

Referring now to FIG. 2A, there is shown a cross sectional view of the spool 185 shown in FIGS. 1 and 2. In FIG. 2A, it is clear that the disk 190 nests with the disk 140 to provide a unitary spool. The conical shaped center 192 nests within the conical cavity in the central hub 142 of disk 140. The spiral shaped interior hub 191 is shown slightly off center in FIG. 2A because of the spiral nature and design thereof. The opening 198 in the spiral shaped interior hub 191 joins with, or accepts, the tubing 193 (see FIG. 2) as shown.

The splines 146 are shown extending outwardly from the external hub 141 of disk 140. The opening 145 which receives the seal 110 (see FIG. 1) is shown in the center of external hub 141. The opening 145 communicates through the opening 195 in conical shaped center 192 with the spiral shaped interior hub 191 and the tubing 193 (as suggested by opening 198).

Referring now to FIG. 3, of the seal/nipple connector 105 shown in FIG. 1. In this case, seal 110 is generally cylindrical in configuration. The hub end 111 thereof is configured to reside and nestle into the opening 145 in the external hub 141 of spool 185. In a preferred embodiment, the seal 110 is fixed to the external hub 141 by suitable adhesive or the like. Thus, the seal 110 becomes, in effect, a part of the spool 185. It is, of course, contemplated that the seal 110 and the spool 185 (or disk 140) can be fabricated as a single unit.

It is also seen that nipple end 112 of seal 110 includes a plurality of concentric rings and shoulders 128 which are used to interlock with the nipple 120.

The nipple 120 includes, at the seal end 122, thereof a plurality of concentric rings and shoulders 129 which interact with the counterpart rings 129 in the nipple end 112. Thus, when the seal 110 is inserted into the nipple 120, the ends 112 and 122 rotatably engage in an interlocking fashion.

The O-ring 130 is, typically, inserted into the seal end 122 and forms a leakproof seal between the inner surface of nipple 120 and the outer surface of seal 110.

The splines 126 on the exterior of nipple 120 are designed to interact with the splines 16 at the drive hub 52 as described supra. The splines 126 are configured in any suitable fashion so as to enhance the efficiency of the interaction and interlocking action between the various splines.

The connector end 121 of nipple 120 includes locking groove 125 which is engaged by the sliding latch 160 as will be described infra. This engagement maintains the spool 185 in connection with the housing 10. The nipple 120 also includes a plurality of concentric ridges 123 which form a groove 124 therebetween. The ridges 123 and groove 124 provide a gripping surface for receiving tubing from some other component such as a pump, reservoir or the like.

While seal 110 and nipple 120 are shown as separate components in this embodiment, it is contemplated that they can be fabricated as single, seal/nipple connector 105.

Referring now to FIG. 4, there is shown a partially broken away view of the motor hub 50 which includes the latching hub 55 and drive hub 52. The latching hub 55 and drive hub 52 (integrally formed as a common motor hub 50) comprise two generally cylindrical hub portions. The outer surface of latching hub 55 includes a plurality of teeth 51 such as gear teeth or the like. The teeth 51 have a suitable number which mates with the hub latch 175 described infra. The appropriate pitch, angle, diameter and so forth are determined by the preferred design requirements. The teeth 51, in this embodiment, are located on the entire outer surface of latching hub 55 which forms the upper cylindrical portion of motor hub 50.

The inner drive hub 52 is also hollow and has a relatively smooth outer surface. A single slot 53 can be provided in the perimeter of drive hub 52 to engage one end of coil spring 20 as shown in FIG. 1. In addition, a plurality of splines 456 are disposed on the inner surface of drive hub 52. The splines 456 are designed to engage the splines 146 in the external hub 141 of spool 185 shown in FIGS. 2 and 2A. Thus, drive hub 52 and spool 185 are selectively engaged for concurrent rotation around the center axis thereof under the influence of the coil spring 20 or the operation of the spool 185 as described.

Figure 5:
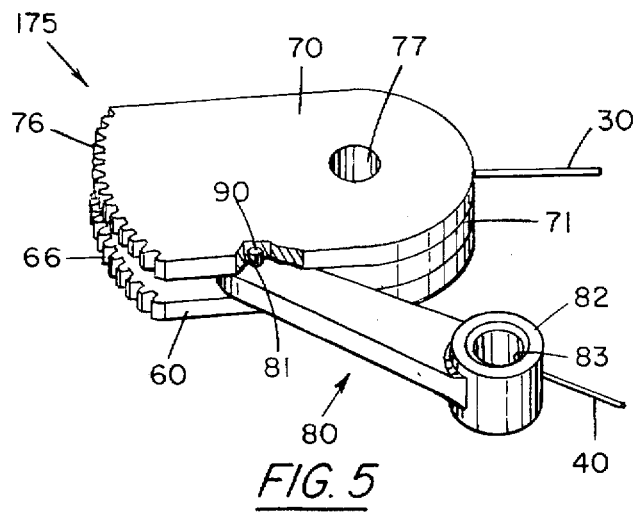
FIG. 5 is a perspective view of the cam mechanism of the instant invention.

Referring now to FIG. 5, there is shown a partially broken away, perspective view of one embodiment of the hub latch 175 of the instant invention.

In this embodiment, the cam mechanism includes the inner latch plate 60 and the outer latch plate 70 which, in this case, includes a spacer 71. The opening 77 passes through latch plate 70 to receive post 275 as described supra. The inner ends of the latch plates 70 and 60 include the toothed edges 76 and 66, respectively. These teeth are arranged to mesh and interact with the teeth 51 of the motor hub 50 shown and described in FIG. 4.

A latch positioning spring 30 is attached to the upper end of the hub latch 175. The spring can be mounted, for example, in an aperture in any of the components 60, 70 or 71.

The cam follower arm 80 has one end thereof disposed intermediate the latch plates 70 and 60. The inner end of cam follower arm 80 is disposed between the bottom of the spacer 71 and the upper edges of the toothed edges 76 and 66. The inner end of cam follower arm 80 includes an aperture 81 therethrough with a pin 90 slidably mounted therein.

The outer end 82 of cam follower arm 80 includes an aperture 83 therethrough which is used to mount the cam follower arm 80 on the post 280 in the retracting mechanism housing 10 as described elsewhere. A cam follower arm positioning spring 40 is mounted to the outer end 82 at the end of cam follower arm 80. The cam follower arm positioning spring 40, similar to the latch positioning spring 30, is a wire spring which positions the cam follower arm 80 in a preferred orientation within the housing 10. The cam follower arm positioning spring 40 is, typically, attached to the cam follower arm 80 by insertion into a suitable aperture formed in the outer end 82 or the like.

It should be noted, that the spacer 71 can be formed as a separate plate or as an integral portion of the inner surface of latch plate 60 or latch plate 70, if so desired.

Figure 6:
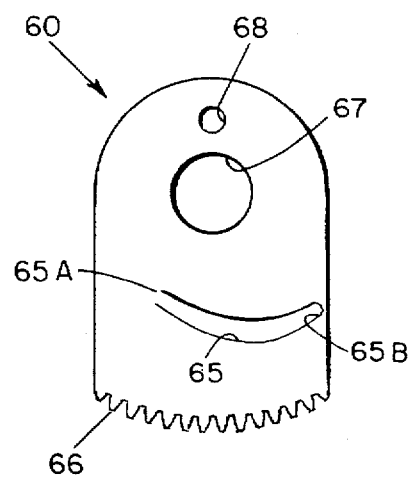
FIG. 6 is a plan view of the inner surface of one portion of the cam.

Referring now to FIG. 6, there is shown the inner surface of the latch plate 60. The toothed edge 66 is shown at one end. The opening 67 is provided to receive the hollow post 74 on latch plate 70. The aperture 68 is provided to receive the post 78 which extends from latch plate 70 (see FIG. 7). The cam groove 65 (which receives the pin 90 of cam follower arm 80 (see FIG. 5) is provided at approximately the midpoint between the mounting opening 67 and the toothed edge 66. The cam groove 65 is arcuate in shape and has a relatively deep recess at end 65B thereof. The arcuate cam groove 65 diminishes in depth until, at end 65A, it is coplanar with the surface of latch plate 60. Thus, cam follower pin 90 riding in cam groove 65 will describe the arcuate path defined by the cam groove 65 and, as well, move from the surface of the latch plate 60 (at end 65A) more deeply into the thickness of latch plate 60 (at end 65B). Thus, the cam follower pin 90 will define an arcuate movement in the plane of the drawing and a vertical movement in a plane perpendicular to the plane of the drawing.

Figure 7:
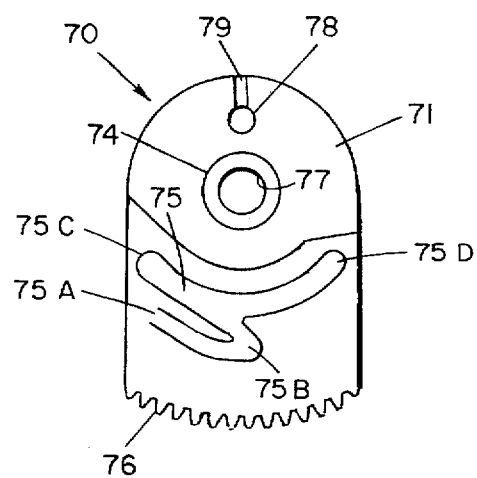
FIG. 7 is a plan view of the inner surface of another portion of the cam.

Referring now to FIG. 7, there is shown the inner surface of latch plate 70 shown above. In FIG. 7, the spacer 71 is also shown inasmuch as the latch plate 70 and the spacer 71 can be formed as an integral component.

The toothed edge 76 of latch plate 70 is described. The hollow post or boss 74 extends from the surface of latch plate 70 and snugly engages opening 67 in latch plate 60. The opening 77 through post 74 is adapted to receive mounting post 275. The post 78 extends from the surface of latch plate 70 and is provided for insertion into aperture 68 in latch plate 60. Thus, the latch plates 60 and 70 are securely positioned by the post 74 and the pin 78. The aperture 79 is provided in axial fashion at the upper end of latch plate 70 in order to receive the latch positioning spring 30 as described above.

The inner surface of latch plate 70 includes a cam groove 75 which has several interconnected arms. The cam groove 75 is juxtaposed with the cam groove 65 in latch plate 60 as shown in FIG. 6 when latch plates 60 and 70 are assembled as hub latch 175.

The cam groove 75 includes an upper portion thereof between ends 75C and 75D which is substantially arcuate. The cam groove 75 also includes a lower portion thereof which is nearly linear between ends 75A and 75B. The upper and lower portions of the groove are interconected by a short arm intermediate ends 75B and 75C. At end 75A, the cam groove 75 is coplanar with the surface of the latch plate 70 similar to the design of groove end 65A in latch plate 60 as described relative to FIG. 6. However, groove ends 65A and 75A are at opposite ends of the common groove formed therebetween when latch plates 60 and 70 are assembled.

The pin 90 is disposed in the common groove wherein cam follower arm 80 follows this path during the extension and/or retraction of the tubing from the spool 185 as described above. That is, in the rest state, the pin 90 of cam follower arm 80 is located in position 75D in the cam groove 75 which coincides with end 65A in cam groove 65. While the tubing is being extended from the spool 185, the spool 185 (through the spline connection) drives drive hub 52 and winds the coil spring 20 around drive hub 52. At the same time, latching hub 55 is rotated and the toothed surface effectively ratchets or rotates freely in the clockwise direction past the toothed edges 66 and 76 of hub latch 175. However, the hub latch 175 is rotated around the axis defined by post 275. As the hub latch 175 is rotated, cam follower arm 80 is, effectively, pulled into the end 75C of cam groove 75.

When the extension of the tubing from the spool is concluded and the pulling force is released, the motor hub 50 is driven by coil spring 20 and the toothed edges of cam follower arm 80 mesh with the teeth 51 on latching hub 55 so that hub latch 175 rotates in the counter clockwise direction. At this time, the pin 90 of cam follower arm 80 rides down the cam groove 75 and comes to rest in the knee 75B of the groove. At this time, the hub latch 175 is locked in position by the cam follower arm 80 and is, therefore, in the locking position relative to motor hub 50 noted above whereupon the hubs 55 and 52, as well as the spool 185, are locked in position.

In order to release the hub latch 175 so that the spool 185 will operate to retract the tubing under the influence of coil spring 20, the tubing is pulled in an extending motion. Thus, spool 185 is rotated and drives motor hub 50 in the counter clockwise motion. The hub latch 175 also moves therewith such that cam follower arm 80 moves along the cam groove to location 75A wherein pin 90 of the cam follower arm 80 is now transferred in a direction which is, essentially, vertical relative to the drawing plane. Thus, the pin 90 is, effectively, transferred to the cam groove 65 in latch plate 60.

Referring concurrently to FIGS. 1, 5, 6, and 7, the cam follower is defined by cam follower arm 80 which includes a pin 90 at one end thereof. The pin 90 is slidably mounted in aperture 81 in cam follower arm 80. The pin extends into the cam groove 65 and/or 75 and follows the respective groove. When the pin reaches the ends 65A and 75A of the respective grooves, the pin has been moved in the vertical plane relative to the drawings as noted and, effectively, transferred to the opposite groove for future operation as described above.

Referring now concurrently to all of the drawings, especially FIG. 1, the operation of the device is clear. The components are assembled as suggested in FIG. 1. The spool 185 is engaged with the mechanism in housing 10 and retained in place by the sliding latch 160 which is slidably mounted in groove 19 formed in the housing by the cover 150. When the tubing 193 (see FIG. 2) is pulled off of the spool 185, the spool rotates in a defined direction, i.e. clockwise or counterclockwise, as desired. This rotation causes the motor hub 50 to rotate. As the motor hub 50 is rotated, a portion of the coil spring 20 is wound onto drive hub 52 and applies a constant torque force thereagainst. As a result of the operation of the hub latch 175, the motor hub 50 is locked in a prescribed position when the tubing is no longer being extracted and the spool 185 is no longer being turned.

In order to return the tubing to the spool, a slight forward motion or extension of the tubing causes the hub latch 175 to interact with latching hub 55 as noted above so that the latching mechanism 175 releases latching hub 55 and permits the coil spring 20 to exert the constant torque force in the opposite direction thereby rotating motor hub 50 in the opposite direction from the extraction mode. Thus, the drive hub 52 which is engaged with the spool 185 causes the spool 185 to rotate in the direction opposite to the extension direction thereby retracting the tubing onto the spool.

As noted, the tubing passes between the spool 185 and the idler roller 180 which, in essence, constrains the tubing to be rewound on the spool 185.

As noted, in order to remove the spool 185 from the mechanism, the sliding latch 160 is activated against the force of latch spring 170 whereupon the locking groove 125 of nipple 120 is released by sliding latch 160. In this case, the spool 185 can be removed from the apparatus housing 10 and other spools or other devices of similar nature can be inserted into the retraction apparatus.

Thus, there is shown and described a unique design and concept of tubing retraction system. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A tubing mechanism comprising, retractor means, and spool means for supporting tubing thereon, said spool means mounted on and driven by said retractor means to retract tubing supported on said spool means, said spool means including first and second substantially parallel disks, each of said disks including a central hub portion, the central hub portion of said first disk including an integral tubular chamber adapted to engage the tubing, the central hub portion of said second disk including a surface adapted to engage a surface of the central hub portion of said first disk, said central hub portion of said second disk including a splined portion thereof which selectively engages said retractor means.

2. The mechanism recited in claim 1 including, connector means joined to said central hub portion of said first disk, said connector means adapted to communicate with said tubular chamber thereby to connect the tubing supported on said spool means to an external source via said tubular chamber.

3. The mechanism recited in claim 2 wherein, said connector means includes a seal and a nipple, said seal is affixed to said central hub portion of said first disk, said nipple is rotatably coupled to said seal.

4. The mechanism recited in claim 3 wherein, said nipple includes at least one end thereof which is adapted to interact with an external source thereby to connect the tubing supported on said spool means to an external source via said tubular chamber.

5. The mechanism recited in claim 2 wherein, said connector means includes locking means for interacting with said retractor means to selectively engage said spool means with said retractor means.

6. The mechanism recited in claim 2 wherein, said connector means includes locking means for interacting with said retractor means to selectively engage said spool means with said retractor means.

7. The mechanism recited in claim 1 wherein, said central hub portion of each of said first and second disks includes a conical portion whereby the conical portion of said first disk nests within the conical portion of said second disk.

8. The mechanism recited in claim 1 wherein, said integral tubular chamber comprises a channel formed in said central hub portion of said first disk and which is adapted to engage the tubing.

9. The mechanism recited in claim 1 wherein, said retractor means includes spring means for engaging and selectively driving said spool means.

10. A tubing mechanism comprising, a tubing retaining spool for supporting tubing thereon, said spool including first and second substantially parallel disks, each of said disks including a central hub portion, the central hub portion of said first disk including an integral tubular chamber adapted to engage the tubing, the central hub portion of said second disk including a surface adapted to engage a surface of the central hub portion of said first disk, said central hub portion of said second disk including a splined portion thereof, retractor means for selectively rotating said spool to retract tubing extended from said spool, said retractor means includes driving means for selectively engaging said splined portion of said second disk of said tubing retaining spool, said driving means includes a motor hub, latching means for selectively latching said motor hub in a prescribed position, said latching means and said motor hub each include at least portions thereof which are toothed whereby the respective toothed portions interact with each other, said latching means includes at least one cam groove therein, and cam follower means which interacts with the cam groove such that said latching means is selectively restrained to a latched position to thereby prevent movement of said motor hub.

11. The mechanism recited in claim 10 including, housing means for enclosing and supporting said driving means.

12. The mechanism recited in claim 11 wherein, said latching means is pivotably mounted in said housing means adjacent to said driving means.

13. The mechanism recited in claim 11 wherein, said latching means is pivotably mounted in said housing means adjacent to said motor hub.

14. The mechanism recited in claim 10 including, a latching hub connected to said motor hub and rotatable therewith, said latching hub arranged to selectively engage said latching means.

15. The mechanism recited in claim 10 including, latch release means operatively connected with said latching means in order to selectively release said motor hub.

16. A tubing mechanism comprising, retractor means, and spool means for supporting flexible tubing, said spool means mounted on and rotatably driven by said retractor means to retract tubing supported on said spool means, said spool means including first and second substantially parallel disks, each of said disks including a central hub portion, the central hub portion of said first disk including an integral tubular chamber adapted to engage the flexible tubing, the central hub portion of said second disk including a surface adapted to engage a surface of the central hub portion of said first disk, said central portion of said second disk including a splined portion thereof, said retractor means including, a motor hub having a splined portion which engages the splined portion of the central hub portion of said second disk, a coil spring which provides a constant torque force to said motor hub for selectively rotating said spool to retract flexible tubing extended from said spool, latching means for selectively latching said motor hub in a prescribed position, and locking means for locking said spool means to said retractor means.

17. The mechanism recited in claim 16 including, connector means joined to said central hub portion of said first disk, said connector means adapted to communicate with said tubular chamber thereby to connect the tubing supported on said spool means to an external source via said tubular chamber.

18. The mechanism recited in claim 17 wherein, said connector means includes a seal and a nipple, said seal affixed to said central hub portion of said first disk, said nipple is rotatably coupled to said seal.

19. The mechanism recited in claim 16 wherein, said central hub portion of each of said first and second disks includes a conical portion whereby said conical portions of the respective disks nest with each other.

20. The mechanism recited in claim 19 wherein, said integral tubular chamber comprises a channel formed in the conical portion of said central hub portion of said first disk and adjacent to the conical portion of said second disk such that said integral tubular chamber is adapted to engage the flexible tubing.

21. The mechanism recited in claim 16 including, housing means for enclosing and supporting said motor hub, said coil spring and said latching means.

22. The mechanism recited in claim 21 wherein, said housing means includes first and second cavities with a communication slot therebetween, said first cavity retains said coil spring therein, said second cavity retains said motor hub therein, said coil spring passes through said communication slot and engages said motor hub.

23. The mechanism recited in claim 21 wherein, said locking means is slidably mounted in said housing means, said locking means includes an aperture therethrough to receive and selectively engage said spool means.

24. The mechanism recited in claim 21 wherein, said housing means includes a mounting end thereof for mounting said housing in a suitable housing support.

25. The mechanism recited in claim 16 including, latch release means operatively connected with said latching means in order to selectively release said motor hub.

26. The mechanism recited in claim 16 wherein, said motor hub includes a drive hub and a latching hub, said drive hub arranged to engage said splined portion of the central portion of said second disk, said latching hub arranged to engage said latching means.

27. The mechanism recited in claim 26 wherein, said drive hub and said latching hub are integrally formed.

28. The mechanism recited in claim 26 wherein, said latching means and said latching hub each include at least portions thereof which are toothed whereby the respective toothed portions interact with each other.

29. The mechanism recited in claim 28 wherein, said latching means includes at least one cam groove therein, and cam follower means which interacts with the cam groove such that said latching means is selectively restrained to a latched position to thereby prevent movement of said latching hub.

* * * * *